United States Patent [19]

Song et al.

[11] Patent Number: 5,968,867
[45] Date of Patent: Oct. 19, 1999

[54] SILICA GEL SUPPORTED BIS-CINCHONA ALKALOID DERIVATIVES AND A PREPARATION METHOD AND USE THEREOF

[75] Inventors: Choong Eui Song, Seoul; Jung Woon Yang, Pusan, both of Rep. of Korea

[73] Assignee: Korea Institute of Science and Technology, Rep. of Korea

[21] Appl. No.: 09/048,275

[22] Filed: Mar. 26, 1998

[30] Foreign Application Priority Data

Sep. 27, 1997 [KR] Rep. of Korea ............... 49388/97
Mar. 13, 1998 [KR] Rep. of Korea ............... 8512/98

[51] Int. Cl.$^6$ ............... B01J 31/00; B01J 21/08; B01J 21/12; B01J 21/14
[52] U.S. Cl. ............... 502/168; 502/151; 502/158; 502/167; 502/233
[58] Field of Search ............... 502/151, 158, 502/167, 168, 233

[56] References Cited

PUBLICATIONS

R. A. Johnson et al, "Catalytic Asymmetric Dihydroxylation" in *Catalytic Asymmetric Synthesis*, I. Ojima ed., VCH Publishers, New York, pp. 227–272, (1993).
H.C. Kolb et al, "Catalytic Asymmetric Dihydroxylation", *Chem. Rev.*, 94, pp. 2483–2547 (1994).
B.B. Lohray, "Recent Advances in the Asymmetric Dihyroxylation of Alkenes", *Tetrahedron: Asymmetry*, vol. 3, No. 11, pp. 1317–1349, (1992).
B.M. Kim et al., "Heterogeneous Catalytic Asymmetric Dihydroxylation: Use of a Polymer–Bound Alkaloid", *Tetrahedron Letters*, vol. 31, No. 21, pp. 3003–3006, (1990).
D. Pini, et al., "Heterogeneous Catalytic Asymmetric Dihydroxylation of Olefins with the OsO$_4$/Poly(9–O–Acylquinine–co–Acrylonitrile) System", *Tetrahedron Letters*, vol. 32, No. 38, pp. 5175–5178, (1991).
D. Pini et al, "A New Crosslinked Polymer for the Heterogeneous Catalytic Asymmetric Dihydroxylation of Alkenes", *Tetrahedron: Asymmetry*, vol. 4, No. 11, pp. 2351–2354 (1993).
B.B. Lohray et al, "Unprecedented Reactivity and Selectivity in Hetrogeneous Asymmetric Catalytic Dihydroxylation of Alkenes", *Tetrahedron Letters*, vol. 35, No. 35, pp. 6559–6562 (1994).
C. Rosini et al., "Cinchona Alkaloids for Preparing New, Easily Accessible Chiral Stationary Phases", *Journal of Chromatography*, 348, pp. 79–87 (1985).

*Primary Examiner*—Mark L. Bell
*Assistant Examiner*—J. Pasterczyk
*Attorney, Agent, or Firm*—Morrison & Foerster

[57] ABSTRACT

The present invention relates to silica gel supported bis-cinchona alkaloid compounds of the formula:

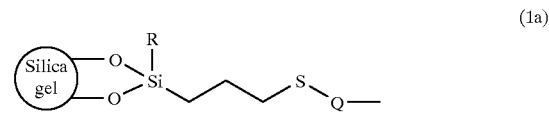
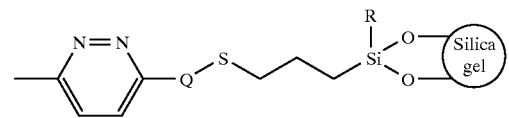

or

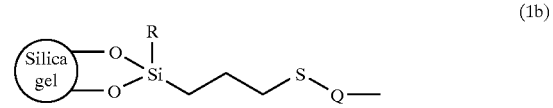
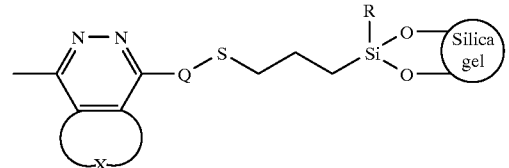

wherein Q is dihydroquininyl or dihydroquinindinyl; X is a compound having 4 carbon atoms; and R is methoxy, ethoxy or methyl; and methods of preparation and use thereof. The silica gel supported bis-cinchona alkaloid derivatives of this invention are useful re-useable catalysts for preparing vicinal diols by asymmetric dihydroxylation of olefins.

10 Claims, No Drawings

SILICA GEL SUPPORTED BIS-CINCHONA ALKALOID DERIVATIVES AND A PREPARATION METHOD AND USE THEREOF

BACKGROUND OF THE INVENTION

The present invention relates to silica gel supported bis-cinchona alkaloid derivatives and a preparation method and use thereof. More particularly, the present invention relates to silica gel supported bis-cinchona alkaloid derivatives of the formula III by chemically reacting formula I as a chiral monomer with silica gel of the formula II. The present invention also relates to the use of the formula I as a catalyst in synthesizing optically-active vicinal diols by asymmetric dihydroxylation reaction of olefins.

The asymmetric dihydroxylation of olefins using catalytic amounts of osmium tetraoxide or potassium osmate dihydrate in the presence of cinchona alkaloid derivatives allows access to a wide variety of optically pure vicinal diols [(a) Johnson, R. A. and Sharpless, K. B. Catalytic Asymmetric Dihydroxylation. In Catalytic Asymmetric Synthesis; Ojima, I., Ed.; VCH publishers: New York, 1993; pp 227–272, (b) Chem. Rev., 1994, 94, 2483–2547, (c) Tetrahedron Asymmetry, 1992, 3, 1317–1349]. However, there are limitations to performing the catalytic AD reaction in synthesizing vicinal diols on a large scale due to the toxicity and high cost of osmium tetraoxide or potassium osmate dihydrate and the cinchona derivatives. By employing the heterogeneous catalytic systems, it was expected to cost-down by using osmium tetroxide and bis-cinchona alkaloids repetitively. To this end, several polymer-bound cinchona alkaloid derivatives have been developed. However, these heterogeneous catalytic systems did not have practical applicability since most of the polymers require complicated synthetic manipulations and, moreover, their catalytic efficiency and enantioselectivity were much worse than those of the homogeneous catalytic systems [(a) Tetrahedron Lett., 1990. 31, 3003, (b) Tetrahedron Lett., 1991, 32, 5175, (c) Tetrahedron Lett., 1992, 33, 5453, (d) Tetrahedron: Asymmetry, 1993, 4, 2351, (e) Tetrahedron Lett., 1994. 35, 6559.

SUMMARY OF THE INVENTION

It is an object of the present invention to develop heterogeneous bis-cinchona alkaloid derivatives that can be prepared by simple procedures, are economical with an improved catalytic efficiency for asymmetric dihydroxylation of olefins, are reusable and have high thermal and mechanical stabilities.

It is another object of the present invention to provide the silica gel supported bis-cinchona alkaloid derivatives.

Further, another object of the present invention is to provide a method of preparing the silica gel supported bis-cinchona alkaloid derivatives.

Another object of the present invention is to provide a method of using the silica gel supported bis-cinchona derivatives as a catalyst in the asymmetric dihydroxylation of olefins.

The manner in which the foregoing and other objects of this invention are accomplished will be apparent from the accompanying specification and claims considered together with the working examples.

DETAILED DESCRIPTION OF THE INVENTION

To achieve the objects described above, new bis-cinchona derivatives represented by the formula I were developed.

formula 1

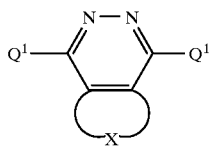

(wherein Q' is quininyl or quinidinyl; X is null or an unsaturated cyclic compound having 4 carbons, and thus forms pyridazine or phthalazine, respectively).

The examples of the bis-cinchona alkaloid derivatives of the formula I are 1,4-bis(9-O-quininyl)phthalazine, 1,4-bis(9-O-quinidinyl)phthalazine), 3,6-bis(9-O-quininyl)pyridazine and 3,6-bis(9-O-quinidinyl)pyridazine of the formulas Ia, Ib, Ic and Id, respectively.

formula 1a

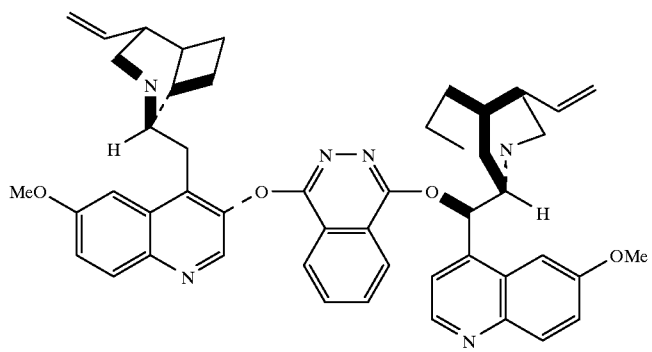

formula 1b

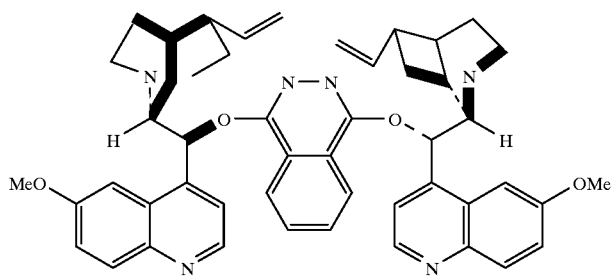

formula 1c

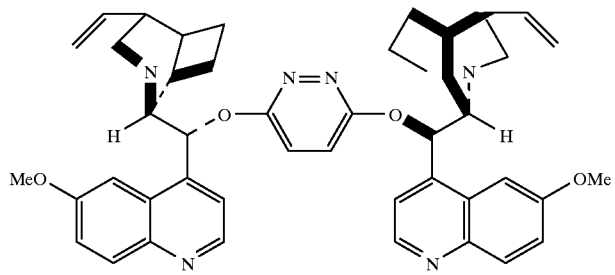

formula 1d

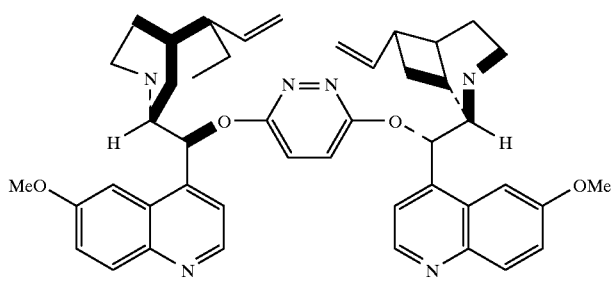

Aforementioned bis-cinchona alkaloid derivatives of the formulas Ia–Id were prepared as follows.

Pure 1,4-bis(9-O-quininyl)phthalazine of the formula Ia was obtained by refluxing 1,4-dichlorophthalazine with quinine in dry toluene in the presence of potassium carbonate and potassium hydroxide.

Pure 1,4-bis(9-O-quinidinyl)phthalazine of the formula Ib was obtained by refluxing 1,4-dichlorophthalazine with quinidine in dry toluene in the presence of potassium carbonate and potassium hydroxide.

Pure 3,6-bis(9-O-quininyl)pyridazine of the formula Ic was obtained by refluxing 3,6-dichloropyridazine with quinine in dry toluene in the presence of potassium carbonate and potassium hydroxide.

Pure 3,6-bis(9-O-quinidinyl)pyridazine of the formula Id was obtained by refluxing 3,6-dichloropyridazine with quinidine in dry toluene in the presence of potassium carbonate and potassium hydroxide.

Following silica gel supported bis-cinchona alkaloid derivatives were prepared by the reaction of chiral monomer of the formula I with mercaptopropylsilanized silica gel of the formula II.

azobisisobutyronitrile (AIBN) as a radical initiator. Pale yellow powder was obtained as a reaction product. The best equivalent weight (Eq. Wt.) ratio between the chiral monomer and the mercaptopropylsilanized silica gel is 1:2 to consider the economical aspects. Mercaptopropylsilanized silica gel of the formula II was prepared by using the similar procedure as described earlier (P. Salvadori, J. Chromatogr., 1985, 348, 79) by reacting silica gel with (3-mercaptopropyl)trimethoxysilane, (3-mercaptopropyl)triethoxysilane or (3-mercaptopropyl)methyldimethoxysilane in the 1:1 (v/v) anhydrous pyridine-toluene mixed-solvent system.

The newly prepared silica gel supported bis-cinchona alkaloid derivatives contain ca. 1 to 3% of nitrogen as indicated by elemental analysis. The mercaptopropylsi-

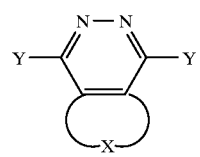

formula I

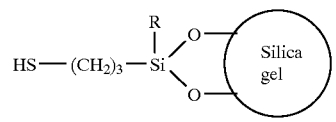

formula II

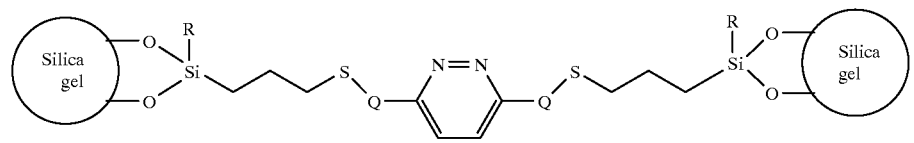

formula III (wherein Q is hydroquininyl or hydroquinindinyl; Q' is quininyl or quinidinyl; X is null or an unsaturated cyclic compound having 4 carbons, and thus forms pyridazine or phthalazine, respectively; and R represents methoxy, ethoxy or methyl).

Detailed description of the preparation method of the silica gel supported bis-cinchona alkaloid derivatives of the formula III is as follows. One of the compounds of the formulas Ia–Id as a chiral monomer was refluxed for two days in chloroform with mercaptopropylsilanized silica gel of the formula II in the presence of 2,2'- lanized silica gel of the formula II can be obtained from any kind of silica gel. However, it is recommended that the adsorbed water should be removed by heating the silica gel to ca. 130~140 ° C. under vacuum (10~0.001 torr).

The silica gel supported bis-cinchona alkaloid derivatives of the formula III can be examplified by the following formulas IIIa, IIIb, IIIc and IIId.

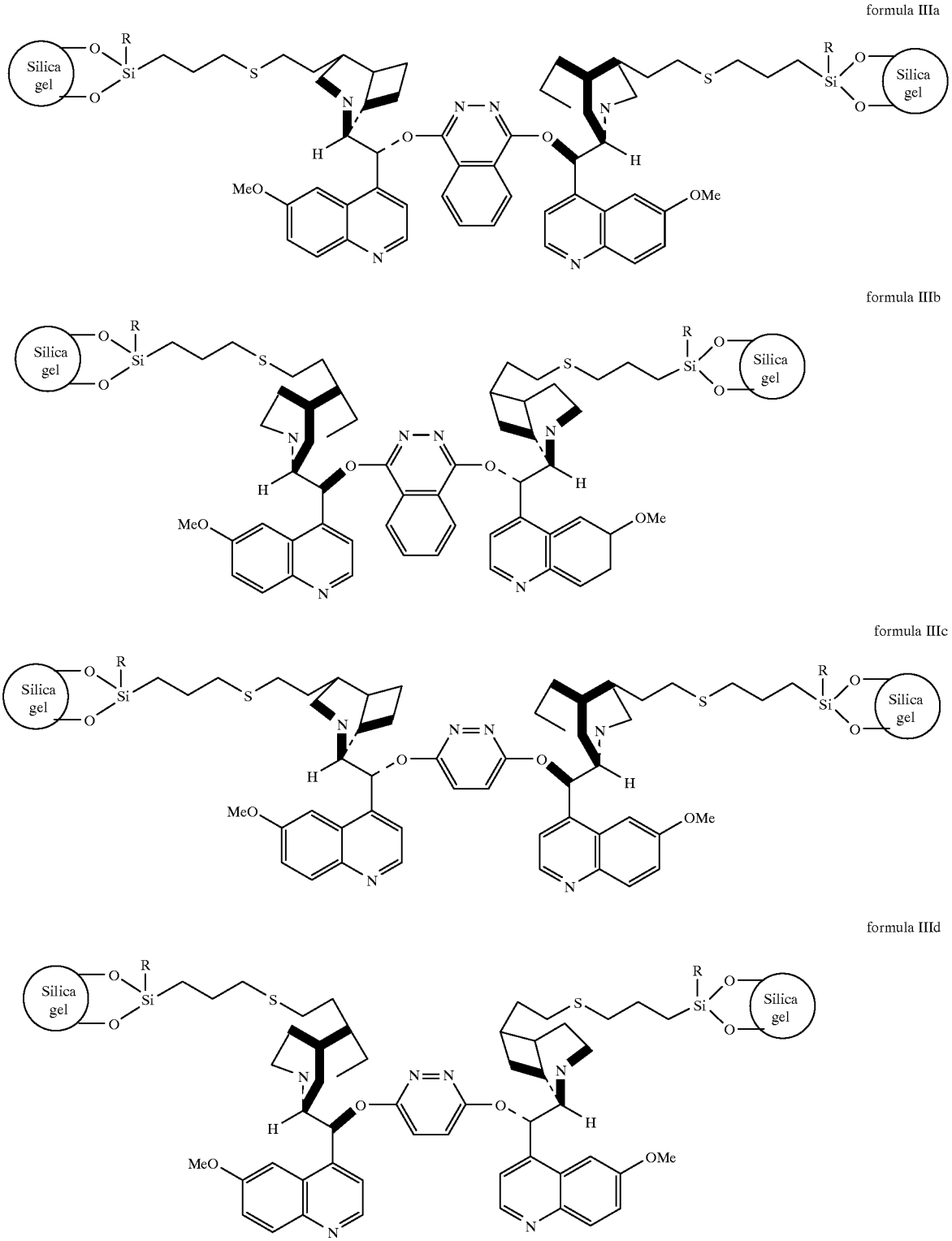

formula IIIa formula IIIb formula IIIc formula IIId (wherein R represents methoxy, ethoxy or methyl; Me is methyl).

The chemicals represented by the formula III of the present invention, i.e., all of the newly prepared silica gel supported bis-cinchona alkaloid derivatives of the formulas Ia–Id, have excellent catalytic efficiency and high enantioselectivity in the asymmetric dihydroxylation reaction of olefins (see Table 1). Moreover, the complex between the silica gel supported bis-cinchona alkaloid derivatives of the formula III and osmium tetraoxide can be separated from the reaction mixture by filtration after the reaction. Therefore, the catalysts can be reusable since the efficiency, especially the enantioselectivity is maintained.

By utilizing the silica gel supported bis-cinchona alkaloid derivatives of the formula III as exemplified by formulas 3a–3d, the catalytic asymmetric dihydroxylation reaction of olefins provides a much simpler and more economical choice than the reaction using the conventional homogeneous catalytic systems.

The invention will be further illustrated by the following examples, but not limited to the examples given.

Preparation of bis-cinchona alkaloid derivatives

EXAMPLE 1

Preparation of 1,4-bis(9-O-guininyl)phthalazine

Formula Ia

To a 500 ml, three-necked, round bottom flask attached with a Dean-Stark condenser, quinine (27.5 g), 1,4-dichlorophthalazine (8.1 g) and potassium carbonate (16.1 g) were dissolved in 300 ml dry toluene. After the two-hour reflux under nitrogen, potassium hydroxide (6.7 g) pellets were added. The reaction continued for 14 hours. The pale orange-colored reaction mixture was cooled to room temperature, washed several times with water and extracted with ethyl acetate. The organic layer was washed with water and brine and dried at reduced pressures to remove the solvent. After the recrystallization with diethylether, pure white solid of 1,4-bis(9-O-quininyl)phthalazine 23.7 g was obtained.

m.p. 159–160° C.

$[\alpha]_D^{23}$+348.4(c 1.08, MeOH)

EXAMPLE 2

Preparation of 1,4-bis(9-O-guinidinyl)phthalazine

Formula Ib

To a 500 ml, three-necked, round bottom flask attached with a Dean-Stark condenser, quinidine (15.6 g), 1,4-dichlorophthalazine (4.8 g) and potassium carbonate (10.2 g) were dissolved in 300 ml dry toluene. After the two-hour reflux under nitrogen, potassium hydroxide (6.75 g) pellets were added. The reaction continued for 14 hours. The pale orange-colored reaction mixture was cooled to room temperature, washed several times with water and extracted with ethyl acetate. The organic layer was washed with water and brine and dried at reduced pressures to remove the solvent. The remainder was dissolved in ethanol and stirred while slowly adding the ethanol solution containing 5% conc. sulfuric acid. While stirring, the sulfate salt of 1,4-bis(9-O-quinidinyl)phthalazine was precipitated. After this salt was filtered and washed with cold ethanol three times, the salt was re-dissolved in water. The pH of the solution was adjusted to ca. 9 to 10 by adding sodium bicarbonate aqueous solution before extracting the product with ethyl acetate. The organic layer was washed with water and dried at reduced pressures to remove the solvent. The product was recrystallized in diethylether to obtain pure 1,4-bis(9-O-quinidinyl)phthalazine 14 g.

m.p. 230–234° C.

EXAMPLE 3

Preparation of 3,6-bis(9-O-guininyl)pyridazine

Formula Ic

To a 1 L, three-necked, round bottom flask attached with a Dean-Stark condenser, quinine (25.0 g), 3,6-dichloropyridazine (5.8 g) and potassium carbonate (16.0 g) were dissolved in 500 ml dry toluene. After the two-hour reflux under nitrogen, potassium hydroxide (6.49 g) pellets were added. The reaction continued for 14 hours. The pale orange-colored reaction mixture was cooled to room temperature, washed several times with water and extracted with ethyl acetate. The organic layer was washed with water and brine and dried at reduced pressures to remove the solvent. The remainder was dissolved in ethanol and stirred while slowly adding the ethanol solution containing 5% conc. sulfuric acid. While stirring, the sulfate salt of the 3,6-bis(9-O-quininyl)pyridazine was precipitated. After this salt was filtered and washed with cold ethanol three times, the salt was dissolved in water. The pH of the solution was adjusted to ca. 9 to 10 by adding sodium bicarbonate aqueous solution before extracting the product with ethyl acetate. The organic layer was washed with water and dried at reduced pressures to remove the solvent to obtain pure 3,6-bis(9-O-quininyl)pyridazine 18 g.

m.p. 134–139° C.

$[\alpha]_D^{23}$+138.5(c 1.06, MeOH)

EXAMPLE 4

Preparation of 3,6-bis(9-O-guinidinyl)pyridazine

Formula Id

To a 1 L, three-necked, round bottom flask attached with a Dean-Stark condenser, quinidine (25.0 g), 3,6-dichloropyridazine (5.8 g) and potassium carbonate (16.0 g) were dissolved in 500 ml dry toluene. After the two-hour reflux under nitrogen, potassium hydroxide (6.49 g) pellets were added. The reaction continued for 14 hours. The pale orange-colored reaction mixture was cooled to room temperature, washed several times with water and extracted with ethyl acetate. The organic layer was washed with water and brine and dried at reduced pressures to remove the solvent. The remainder was dissolved in ethanol and stirred while slowly adding the ethanol solution containing 5% conc. sulfuric acid. While stirring, the sulfate salt of the 3,6-bis(9-O-quininyl)pyridazine was precipitated. After this salt was filtered and washed with cold ethanol three times, the salt was dissolved in water. The pH of the solution was adjusted to ca. 9 to 10 by adding sodium bicarbonate aqueous solution before extracting the product with ethyl acetate. The organic layer was washed with water and dried at reduced pressures to remove the solvent to obtain pure 3,6-bis(9-O-quinidinyl)pyridazine 16 g.

m.p. 160–164 C $[\alpha]_D^{23}$-97.2 (c 1.08, MeOH)

EXAMPLE 5

Preparation of Silica Gel Supported Bis-cinchona Alkaloid Derivatives

Formula 3a

Example 5.1

Preparation of the compound wherein R=methoxy of the formula IIIa

Silica gel (21 g) was treated with 90 ml of (3-mercaptopropyl) trimethoxysilane in 180 ml of anhydrous pyridine/toluene. The slurry was heated at 90° C. for 24 hours. After filtration the solid was washed sequentially with toluene, acetone, ether and pentane and dried under vacuum for 1 hr, resulting in 24.5 g of a mercaptopropyl silanized silica gel derivative, wherein R is methoxy, of formula II containing 1.12 mmol of S per gram of derivatized silica. This mercaptopropyl silanized silica gel derivative, wherein R is methoxy, of formula II (6 g) was suspended in 100 ml chloroform and refluxed with the chiral monomer, 1,4-bis(9-O-quininyl)phthalazine (1.7 g) of formula Ia in the presence of AIBN (165 mg) for 48 hours. Again, after filtration, the solid was washed exhaustively with dichloromethane, ethyl acetate and methanol until the 1,4-bis(9-O-quininyl) phthalazine in excess was completely removed and dried under vacuum. Elemental analysis showed that the product contains 1.72% of nitrogen. This means that 0.20 mmol of the alkaloid of formula Ia is incorporated per 1 gram of the product.

Example 5.2

Preparation of the compound wherein R=ethoxy of the formula IIIa

Silica gel (21 g) was treated with 90 ml of (3-mercaptopropyl) trimethoxysilane in 180 ml of anhydrous pyridine/toluene. The slurry was heated at 90° C. for 24 hours. After filtration the solid was washed sequentially with toluene, acetone, ether and pentane and dried under vacuum for 1 hr, resulting in 26 g of a mercaptopropyl silanized silica gel derivative, wherein R is ethoxy, of formula II containing 1.32 mmol of S (sulfur) per gram of derivatized silica. This mercaptopropyl silanized silica gel derivative, wherein R is ethoxy, of formula II (6 g) was suspended in 100 ml chloroform and refluxed with the chiral monomer, 1,4-bis(9-O-quininyl)phthalazine (1.7 g) of formula Ia in the presence of AIBN (165 mg) for 48 hours. Again, after filtration, the solid was washed exhaustively with dichloromethane, ethyl acetate and methanol until the 1,4-bis(9-O-quininyl) phthalazine in excess was completely removed and dried under vacuum. Elemental analysis showed that the product contains 1.90% of nitrogen. This means that 0.22 mmol of the alkaloid of formula Ia is incorporated per 1 gram of the product.

Example 5.3

Preparation of the compound wherein R=methyl of the formula IIIa

Silica gel (21 g) was treated with 90 ml of (3-mercaptopropyl) trimethoxysilane in 180 ml of anhydrous pyridine/toluene. The slurry was heated at 90° C. for 24 hours. After filtration the solid was washed sequentially with toluene, acetone, ether and pentane and dried under vacuum for 1 hr, resulting in 26.1 g of a mercaptopropyl silanized silica gel derivative, wherein R is methyl, of formula II containing 1.36 mmol of S per gram of derivatized silica. This mercaptopropyl silanized silica gel derivative, wherein R is methyl, of formula II (6 g) was suspended in 100 ml chloroform and refluxed with the chiral monomer, 1,4-bis(9-O-quininyl)phthalazine (1.7 g) of formula Ia in the presence of AIBN (165 mg) for 48 hours. Again, after filtration, the solid was washed exhaustively with dichloromethane, ethyl acetate and methanol until the 1,4-bis(9-O-quininyl) phthalazine in excess was completely removed and dried under vacuum. Elemental analysis showed that the product contains 1.52% of nitrogen. This means that 0.18 mmol of the alkaloid of formula Ia is incorporated per 1 gram of the product.

EXAMPLE 6

Preparation of Silica Gel Supported Bis-cinchona Alkaloid Derivatives

Formula 3b

Example 6.1 Preparation of the compound wherein R=methoxy of the formula IIIb The silica gel derivative (6 g) of the formula II wherein R is methoxy in Example 5.1 and the chiral monomer, 1,4-bis(9-O-quinidinyl)phthalazine (1.7 g) of the formula Ib were refluxed for 48 hours in 100 ml chloroform in the presence of AIBN (165 mg). After filtration, the solid was washed exhaustively with dichloromethane, ethyl acetate and methanol until the 1,4-bis(9-O-quinidinyl) phthalazine in excess was completely removed and dried under vacuum. Elemental analysis showed that the product contains 1.94% of nitrogen. This means that 0.23 mmol of the alkaloid of formula Ib is incorporated per 1 gram of the product.

Example 6.2

Preparation of the compound wherein R=ethoxy of the formula IIIb

The silica gel derivative (6 g) of the formula II wherein R is ethoxy in Example 5.2 and the chiral monomer, 1,4-bis(9-O-quinidinyl)phthalazine (1.7 g) of the formula Ib were refluxed for 48 hours in 100 ml chloroform in the presence of AIBN (165 mg). After filtration, the solid was washed exhaustively with dichloromethane, ethyl acetate and methanol until the 1,4-bis(9-O-quinidinyl) phthalazine in excess was completely removed and dried under vacuum. Elemental analysis showed that the product contains 1.34% of nitrogen. This means that 0.16 mmol of the alkaloid of formula Ib is incorporated per 1 gram of the product.

Example 6.3

Preparation of the compound wherein R=ethoxy of the formula IIIb

The silica gel derivative (6 g) of the formula II wherein R is methyl in Example 5.3 and the chiral monomer, 1,4-bis(9-O-quinidinyl)phthalazine (1.7 g) of the formula Ib were refluxed for 48 hours in 100 ml chloroform in the presence of AIBN (165 mg). After filtration, the solid was washed exhaustively with dichloromethane and methanol until the 1,4-bis(9-O-quinidinyl)phthalazine in excess was completely removed and dried under vacuum. Elemental analysis showed that the product contains 2.01% of nitrogen. This means that 0.24 mmol of the alkaloid of formula Ib is incorporated per 1 gram of the product.

EXAMPLE 7

Preparation of Silica Gel Supported Bis-cinchona Alkaloid Derivatives

Formula 3c

Example 7.1

Preparation of the compound wherein R=methoxy of the formula IIIc

The silica gel derivative (6 g) of the formula II wherein R is methoxy in Example 5.1 and the chiral monomer, 3,6-bis(9-O-quininyl)pyridazine (1.5 g) of the formula Ic were refluxed for 48 hours in 100 ml chloroform in the presence of AIBN (165 mg). After filtration, the solid was washed exhaustively with dichloromethane, ethylacatate and methanol until the 3,6-bis(9-O-quininyl)pyridazine in excess was completely removed and dried under vacuum. Elemental analysis showed that the product contains 1.53% of nitrogen. This means that 0.18 mmol of the alkaloid of formula Ic is incorporated per 1 gram of the product.

Example 7.2

Preparation of the compound wherein R=ethoxy of the formula IIIc

The silica gel derivative (6 g) of the formula II wherein R is ethoxy in Example 5.2 and the chiral monomer, 3,6-bis(9-O-quininyl)pyridazine (1.5 g) of the formula Ic were refluxed for 48 hours in 100 ml chloroform in the presence of AIBN (165 mg). After filtration, the solid was washed exhaustively with dichloromethane, ethyl acetate and methanol until the 3,6-bis(9-O-quininyl)pyridazine in excess was completely removed and dried under vacuum. Elemental analysis showed that the product contains 2.15% of nitrogen. This means that 0.25 mmol of the alkaloid of formula Ic is incorporated per 1 gram of the product.

Example 7.3

Preparation of the compound wherein R=methyl of the formula 3c

The silica gel derivative (6 g) of the formula II wherein R is methyl in Example 5.3 and the chiral monomer, 3,6-bis(9-O-quininyl)pyridazine (1.5 g) of the formula Ic were refluxed for 48 hours in 100 ml chloroform in the presence of AIBN (165 mg). After filtration, the solid was washed exhaustively with dichloromethane, ethylacatate and methanol until the 3,6-bis(9-O-quininyl)pyridazine in excess was completely removed and dried under vacuum. Elemental analysis showed that the product contains 1.22% of nitrogen. This means that 0.14 mmol of the alkaloid of formula Ic is incorporated per 1 gram of the product.

EXAMPLE 8

Preparation of Silica Gel Supported Bis-cinchona Alkaloid Derivatives

Formula 3d

Example 8.1

Preparation of the compound wherein R=methoxy of the formula IIId

The silica gel derivative (6 g) of the formula II wherein R is methoxy in Example 5.1 and the chiral monomer 3,6-bis(9-O-quinidinyl)pyridazine (1.5 g) of the formula Id were refluxed for 48 hours in 100 ml chloroform in the presence of AIBN (165 mg). After filtration, the solid was washed exhaustively with dichloromethane, ethyl acetate and methanol until the 3,6-bis(9-O-quinidinyl) pyridazine in excess was completely removed and dried under vacuum. Elemental analysis showed that the product contains 1.78% of nitrogen. This means that 0.21 mmol of the alkaloid of formula Id is incorporated per 1 gram of the product.

Example 8.2

Preparation of the compound wherein R=ethoxy of the formula IIId

The silica gel derivative (6 g) of the formula II wherein R is ethoxy in Example 5.2 and the chiral monomer, 3,6-bis(9-O-quinidinyl)pyridazine (1.5 g) of the formula Id were refluxed for 48 hours in 100 ml chloroform in the presence of AIBN (165 mg). After filtration, the solid was washed exhaustively with dichloromethane, ethyl acetate and methanol until the 3,6-bis(9-O-quinidinyl) pyridazine in excess was completely removed and dried under vacuum. Elemental analysis showed that the product contains 1.84% of nitrogen. This means that 0.22 mmol of the alkaloid of formula Id is incorporated per 1 gram of the product.

Example 8.3

Preparation of the compound wherein R=methyl of the formula IIId

The silica gel derivative (6 g) of the formula II wherein R is methyl in Example 5.3 and the chiral monomer, 3,6-bis(9-O-quinidinyl)pyridazine (1.5 g) of the formula Id were refluxed for 48 hours in 100 ml chloroform in the presence of AIBN (165 mg). After filtration, the solid was washed exhaustively with dichloromethane, ethyl acetate and methanol until the 3,6-bis(9-O-quinidinyl) pyridazine in excess was completely removed and dried under vacuum. Elemental analysis showed that the product contains 1.88% of nitrogen. This means that 0.22 mmol of the alkaloid of formula Id is incorporated per 1 gram of the product.

Catalytic Effect of the Compound of the Formula III in the Present Invention in the Asymmetric Dihydroxylation Reaction of Olefins To prove the catalytic effect of the silica gel supported bis-cinchona alkaloids of the formula III in the present invention, the asymmetric dihydroxylation reaction of olefins was performed by using the following two methods according to the literature [(a) Johnson, R. A. and Sharpless, K. B. "Catalytic Asymmetric Synthesis", Ojima, I. (Ed.);

VCH publishers, Inc.: 227–272 (b) Kolb, H. C.; VanNieuwenhze, M. S.; Sharpless, K. B. Chem. Rev. 1994, 94, 2483–2547].

The first condition in proving the catalytic effect in the asymmetric dihydroxylation of olefins in the present invention is as follows.

Bis-cinchona alkaloid of the formulas IIIa–IIId (0.002~0.10 equivalent weight of alkaloid content in the silica gel), potassium ferricyanide ($K_3Fe(CN)_6$, 3.0 equivalent weight (Eq. Wt.) and potassium carbonate ($K_2CO_3$, 3.0 Eq. Wt.) were stirred for 10 min in the mixed solvent of tert-butanol/water (in the volume ratio of 1:1 or 1:2). Two (2) percent of osmium tetraoxide aqueous solution (0.002~0.02 Eq. Wt) was added in the mixture, and the mixture was stirred for additional 30 min. Olefin (1.0 Eq. Wt) and methanesulfonamide (1.0 Eq. Wt) were added to the mixture. After the reaction, the slurry was filtered to separate the complex between bis-cinchona alkaloid of the formula 3a–3d and osmium tetraoxide from the filtrate. After sodium sulfite (1.5 Eq. Wt.) was added to the filtrate and stirred for an hour, pure product was separated by using conventional separation processes. The yield and the optical purity of the product were determined.

The second condition in proving the catalytic effect in the asymmetric dihydroxylation of olefins in the present invention is as follows.

Bis-cinchona alkaloid of the formula 3a–3d (0.002~0.25 Eq. Wt. of alkaloid content in the silica gel) and N-methylmorpholine-N-oxide (1.5 Eq. Wt.) were stirred for 10 min in the mixed solvent of acetone/water (in the volume ratio of 10:1). Two (2) percent of osmium tetraoxide aqueous solution (0.002~0.02 Eq. Wt.) was added in the mixture, and the mixture was stirred for additional 30 min. Olefin (1.0 Eq. Wt) and tetraethylammoniumacetate (1.0 Eq. Wt) were added to the mixture. After the reaction, the slurry was filtered to obtain the complex between bis-cinchona alkaloid of the formula 3a–3d and osmium tetraoxide from the filtrate. After sodium sulfite (1.5 Eq. Wt.) was added to the filtrate and stirred for an hour, pure product was separated by using conventional separation processes. The yield and the optical purity of the product were determined.

EXAMPLE 9
Catalytic asymmetric dihydroxylation reaction of olefins by using silica gel supported bis-cinchona alkaloid derivatives of the formulas 3a–3d

Example 9.1
Method of using potassium ferricyanide as a co-oxidant in the asymmetric dihydroxylation Silica gel supported bis-cinchona alkaloid derivatives of the formulas 3a–3d (0.02 Eq. Wt.), potassium ferricyanide (3.0 Eq. Wt.), potassium carbonate (3.0 Eq. Wt.) were stirred for 10 min in the mixed solvent of tert-butanol/water (in the volume ratio of 1:2). Two (2) percent of osmium tetraoxide aqueous solution (0.01 Eq. Wt) was added in the mixture, and the mixture was stirred for additional 2 hours. Olefin (1.0 Eq. Wt) and methanesulfonamide (1.0 Eq. Wt) were added to the mixture. Silica gel supported bis-cinchona alkaloid was filtered out after the reaction. Sodium metabisulfite (1.5 Eq. Wt.) was added to the filtrate and stirred for an hour. The organic layer was extracted with ethyl acetate and was washed exhaustively with water before drying. Solvent was removed at reduced pressures. Pure product was obtained by performing the column chromatography.

Example 9.1.1
Catalytic asymmetric dihydroxylation reaction of trans-stilbene by using bis-cinchona alkaloid of the formula IIIa wherein R is methoxy The reaction was performed by using an identical process as in Example 9.1 with a reaction time of 25 hours. (S,S)-(−)-1,2-diphenyl-1,2-ethanediol of more than 99.0% of enantiomeric excess was obtained (yield 88%)

$[\alpha]_D$ −92.12 (c 0.99, EtOH): e.e.=99.1%

Example 9.1.2
Catalytic asymmetric dihydroxylation reaction of trans-(β-methyl styrene by using bis-cinchona alkaloid of the formula IIIa wherein R is methoxy The reaction was performed by using an identical process as in Example 9.1 with a reaction time of 25 hours. (S,S)-phenylmethane-1,2-ethanediol of more than 96.0% of enantiomeric excess was obtained (yield 92%)

$[\alpha]_D$ +30.00 (c 1.32, EtOH): e.e.=96.5%

Example 9.1.3
Catalytic asymmetric dihydroxylation reaction of methyl trans-cinnamate by using bis-cinchona alkaloid of the formula IIIa wherein R is methoxy The reaction was performed by using an identical process as in Example 9.1 with a reaction time of 20 hours. (2R, 3S)-2,3-dihydroxy-3-phenylpropionate of more than 95.0% of enantiomeric excess was obtained (yield 93%)

$[\alpha]_D$ +10.19 (c 1.03, $CHCl_3$): e.e.=95.2%

Example 9.1.4
Catalytic asymmetric dihydroxylation reaction of 1-phenyl-1-cyclohexene by using bis-cinchona alkaloid of the formula IIIa wherein R is methoxy The reaction was performed by using an identical process as in Example 9.1 with a reaction time of 15 hours. (S,S)-1-phenyl-1,2-cyclohexanediol of more than 96.0% of enantiomeric excess was obtained (yield 96%)

$[\alpha]_D$ −18.56 (c 1.11, $C_6H_6$): e.e.=96.2%

Example 9.1.5
Catalytic asymmetric dihydroxylation reaction of 1-phenyl-1-cyclohexene by using bis-cinchona alkaloid of the formula IIIa wherein R is methoxy which had been used in Example 9.1.4. without further addition of osmium tetraoxide The reaction was performed by using an identical process as in Example 9.1 with a reaction time of 21 hours. (S,S)-1-phenyl-1,2-cyclohexanediol of more than 92.0% of enantiomeric excess was obtained (yield 92%)

$[\alpha]_D$ −17.77 (c 1.03, $C_6H_6$): e.e.=92.1%

Example 9.1.6
Catalytic asymmetric dihydroxylation reaction of 1-phenyl-1-cyclohexene by using bis-cinchona alkaloid of the formula IIIa wherein R is methoxy which had been used in Example 9.1.5 without further addition of osmium tetraoxide The reaction was performed by using an identical process as in Example 9.1 with a reaction time of 28 hours. (S,S)-1-phenyl-1,2-cyclohexanediol of more than 89.0% of enantiomeric excess was obtained (yield 36%)

$[\alpha]_D$ −17.10 (c 1.00, $C_6H_6$): e.e.=89.1%

Example 9.1.7
Catalytic asymmetric dihydroxylation reaction of 1-phenyl-1-cyclohexene by using bis-cinchona alkaloid of the formula IIIa wherein R is methoxy The reaction was performed by using an identical process as in Example 9.1 except that the Eq. Wt. ratio between the reactants were olefin:osmium tetraoxide:bis-cinchona alkaloid derivative wherein R is methoxy of the formula IIIa was 1:0.01:0.01 with a reaction time of 21 hours. (S,S)-1-phenyl-1,2-cyclohexanediol of more than 94.0% of enantiomeric excess was obtained (yield 95%)

$[\alpha]_D$ −18.30 (c 1.06, $C_6H_6$): e.e.=94.8%

Example 9.1.8
Catalytic asymmetric dihydroxylation reaction of 1-phenyl-1-cyclohexene by using bis-cinchona alkaloid of the formula IIIa wherein R is methoxy The reaction was performed by using an identical process as in Example 9.1 except that the Eq. Wt. ratio between the reactants were olefin:osmium tetraoxide:bis-cinchona alkaloid derivative wherein R is methoxy of the formula IIIa was 1:0.002:0.02 with a reaction time of 22 hours. (S,S)-1-phenyl-1,2-cyclohexanediol of more than 85.0% of enantiomeric excess was obtained (yield 93%)

$[\alpha]_D$ −16.52 (c 1.03, $C_6H_6$): e.e.=85.6%

Example 9.1.9
Catalytic asymmetric dihydroxylation reaction of trans-stilbene by using bis-cinchona alkaloid of the formula IIIb wherein R is ethoxy The reaction was performed by using an identical process as in Example 9.1 with a reaction time of 26 hours. (R,R)-(+)-1,2-diphenyl-1,2-ethandiol of more than 98.0% of enantiomeric excess was obtained (yield 85%)

$[\alpha]_D$ +91.33 (c 1.15, EtOH): e.e.=98.2%

Example 9.1.10
Catalytic asymmetric dihydroxylation reaction of trans-cinnamate by using bis-cinchona alkaloid of the formula IIIb wherein R is ethoxy The reaction was performed by using an identical process as in Example 9.1 with a reaction time of 19 hours. (2S, 3R)-dihydroxy-3-phenylpropionate of more than 95.0% of enantiomeric excess was obtained (yield 95%)

$[\alpha]_D$ −10.16 (c 1.06, $CHCl_3$): e.e.=95.0%

Example 9.1.11
Catalytic asymmetric dihydroxylation reaction of trans-(β-methyl styrene by using bis-cinchona alkaloid of the formula IIIc wherein R is methoxy The reaction was performed by using an identical process as in Example 9.1 with a reaction time of 15 hours. (S,S)-phenylmethane-1,2-diol of more than 96.0% of enantiomeric excess was obtained (yield 94%)

$[\alpha]_D$ +29.89 (c 1.12, EtOH): e.e.=96.1%

Example 9.1.12
Catalytic asymmetric dihydroxylation reaction of 1-phenyl-1-cyclohexene by using bis-cinchona alkaloid of the formula IIIc wherein R is methoxy The reaction was performed by using an identical process as in Example 9.1 with a reaction time of 15 hours. (S,S)-1-phenyl-1,2-cyclohexanediol of more than 96.0% of enantiomeric excess was obtained (yield 96%)

$[\alpha]_D$ −18.70 (c 1.02, $C_6H_6$): e.e.=96.9%

Example 9.1.13
Catalytic asymmetric dihydroxylation reaction of trans-(β-methyl styrene by using bis-cinchona alkaloid of the formula IIId wherein R is methyl The reaction was performed by using an identical process as in Example 9.1 with a reaction time of 15 hours. (R,R)-phenylmethane-1,2-diol of more than 94.0% of enantiomeric excess was obtained (yield 95%)

$[\alpha]_D$ −29.39 (c 1.42, EtOH): e.e.=94.5%

Example 9.1.14
Catalytic asymmetric dihydroxylation reaction of 1-phenyl-1-cyclohexene by using bis-cinchona alkaloid of the formula IIId wherein R is methyl The reaction was performed by using an identical process as in Example 9.1 with a reaction time of 15 hours. (R,R)-1-phenyl-1,2-cyclohexanediol of more than 95.0% of enantiomeric excess was obtained (yield 97%)

$[\alpha]_D$ +18.37 (c 1.05, $C_6H_6$): e.e.=95.2%

The experimental results in the Examples 9.1.1 through 9.1.14 were tabulated in Table 1.

Example 9.2
Asymmetric dihydroxylation reaction using N-methylmorpholine-N-oxide as a co-oxidant Silica gel supported bis-cinchona alkaloid (0.1 Eq. Wt.) and N-methylmorpholine-N-oxide (1.5 Eq. Wt.) were stirred for 10 min in the mixed solvent of acetone/water (in the volume ratio of 10:1). Two (2) percent of osmium tetraoxide aqueous solution (0.01 Eq. Wt) was added in the mixture, and the mixture was stirred for additional 30 min. Olefin (1.0 Eq. Wt) and tetraethylammoniumacetate (1.0 Eq. Wt) were added to the mixture. After the reaction, the slurry was filtered to separate the complex between bis-cinchona alkaloid of the formula 3a–3d and osmium tetraoxide from the filtrate. After sodium sulfite (1.5 Eq. Wt.) was added to the filtrate and stirred for an hour, the organic layer was extracted out. The extracted organic layer was washed exhaustively with water and dried. The pure compound was obtained by removing the solvent at reduced pressure followed by column chromatography.

Example 9.2.1
Catalytic asymmetric dihydroxylation reaction of trans-stilbene by using bis-cinchona alkaloid of the formula IIIa wherein R is methoxy The reaction was performed by using an identical process as in Example 9.2 with a reaction time of 24 hours. (S,S)-(−)-1,2-diphenyl-1,2-ethandiol of more than 82.0% of enantiomeric excess was obtained (yield 80%)

$[\alpha]_D$ −76.82 (c 1.07, EtOH): e.e.=82.6%

Example 9.2.2
Catalytic asymmetric dihydroxylation reaction of trans-cinnamate by using bis-cinchona alkaloid of the formula IIIa wherein R is methoxy The reaction was performed by using an identical process as in Example 9.2 with a reaction time of 22 hours. (2R, 3S)-2,3-dihydroxy-3-phenylpropionate of more than 83.0% of enantiomeric excess was obtained (yield 83%)

$[\alpha]_D$ +8.89 (c 1.03, $CHCl_3$): e.e.=83.1%

TABLE 1

Catalytic asymmetric dihydroxylation
reaction of olefins by using bis-cinchona alkaloids of the formulas 3a–3d

| Example No. | Bis-chinchna alkaloid | olefin | Reac. time | $[\alpha]_D^{20}$ (C, solvent) | Yield[b] % | e.e.[c] % | Config.[c] |
|---|---|---|---|---|---|---|---|
| 9.1.1 | 3a (R = OMe) | Ph-CH=CH-Ph | 25 h | −92.12 (0.99, EtOH) | 88 | >99 | S,S |
| 9.1.2 | 3a (R = OMe) | Ph-CH=CH-CH₃ | 15 h | +30.00 (1.32, EtOH) | 92 | 96.5 | S,S |
| 9.1.3 | 3a (R = OMe) | Ph-CH=CH-CO₂Me | 20 h | +10.19 (1.03, CHCl₃) | 93 | 95.2 | 2R,3S |
| 9.1.4 | 3a (R = OMe) | 1-phenylcyclohexene | 15 h | −18.56 (1.11, C₆H₆) | 96 | 96.2 | S,S |
| 9.1.5[d] | 3a (R = OMe) | 1-phenylcyclohexene | 21 h | −17.77 (1.03, C₆H₆) | 92 | 92.1 | S,S |
| 9.1.6[e] | 3a (R = OMe) | 1-phenylcyclohexene | 28 h | −17.10 (1.00, C₆H₆) | 36 | 89.1 | S,S |
| 9.1.7[f] | 3a (R = OMe) | 1-phenylcyclohexene | 16 h | −18.30 (1.05, C₆H₆) | 95 | 94.8 | S,S |
| 9.1.8[g] | 3a (R = OMe) | 1-phenylcyclohexene | 22 h | −16.52 (1.03, C₆H₆) | 93 | 85.6 | S,S |
| 9.1.9 | 3b (R = OMe) | Ph-CH=CH-Ph | 26 h | +91.33 (1.15, EtOH) | 85 | 98.2 | R,R |
| 9.1.10 | 3b (R = OEt) | Ph-CH=CH-CO₂Me | 19 h | −10.16 (1.06, CHCl₃) | 95 | 95.0 | 2S,3R |
| 9.1.11 | 3c (R = OMe) | Ph-CH=CH-CH₃ | 15 h | +29.89 (1.12, EtOH) | 94 | 96.1 | S,S |
| 9.1.12 | 3c (R = OMe) | 1-phenylcyclohexene | 15 h | −18.70 (1.02, C₆H₆) | 96 | 96.9 | S,S |

TABLE 1-continued

Catalytic asymmetric dihydroxylation reaction of olefins by using bis-cinchona alkaloids of the formulas 3a–3d

| Example No. | Bis-chinchna alkaloid | olefin | Reac. time | $[\alpha]_D^{20}$ (C, solvent) | Yield[b] % | e.e.[c] % | Config.[c] |
|---|---|---|---|---|---|---|---|
| 9.1.13 | 3d (R = OMe) | Ph⁀⁀ | 15 h | −29.39 (1.42, EtOH) | 95 | 94.5 | R,R |
| 9.1.14 | 3d (R = OMe) | (cyclohexenyl-Ph) | 15 h | +18.37 (1.05, C₆H₆) | 97 | 95.2 | R,R |

[a]Equivalent weight ratio of the reactants = olefin:osmium tetraoxide:silica gel supported bis-cinchona alkaloid derivative = 1:0.01:0.02, reaction temperature 10° C.
[b]Yield percent after the separation by using column chromatography.
[c]% e.e.(e.e. means enantiomeic excess)and absolute configuration were compared with the $[\alpha]_D$ values in the literature.
[d]Reaction performed by re-using the bis-cinchona alkaloid of the formula IIIa that was used in Example 9.1.4. without further addition of osmium tetraoxide.
[e]Reaction performed by re-using the bis-cinchona alkaloid of the formula IIIa that was used in Example 9.1.5. without further addition of osmium tetraoxide.
[f]Equivalent weight ratio of the reactants = olefin:osmium tetraoxide:bis-cinchona alkaloid derivative of the formula III = 1:0.01:0.01.
[g]Equivalent weight ratio of the reactants = olefin:osmium tetraoxide:bis-cinchona alkaloid derivative of the formula III = 1:0.002:0.02.

As shown in Table 1 above, the new derivatives of the formulas IIIa–IIId showed excellent reactivity and enantioselectivity. Moreover, the complex between osmium tetraoxide and bis-cinchona alkaloid derivatives of the formulas IIIa–IIId could be filtered easily. When this compound was reused in the reaction, the catalytic efficiency, particularly the optical selectivity was nearly retained.

In conclusion, the asymmetric dihydroxylation reaction of olefins can be performed much more economically by using the newly developed bis-cinchona alkaloid derivatives of the formulas IIIa–IIId of the present invention than by using the conventional homogeneous catalytic systems.

What is claimed is:

1. Silica gel supported bis-cinchona alkaloid compounds of the formula:

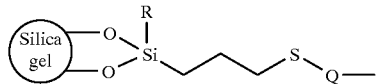
(1a)

-continued

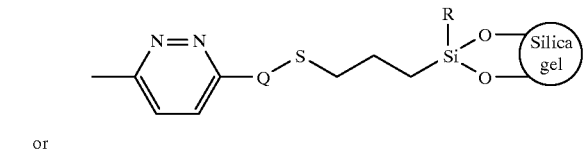

or

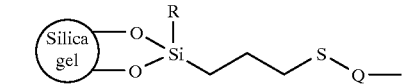
(1b)

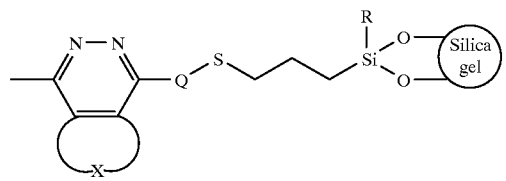

wherein Q is hydroquininyl or hydroquinindinyl; X is a moiety having 4 carbon atoms; and R is methoxy, ethoxy or methyl.

2. A compound according to claim 1 having the formula:
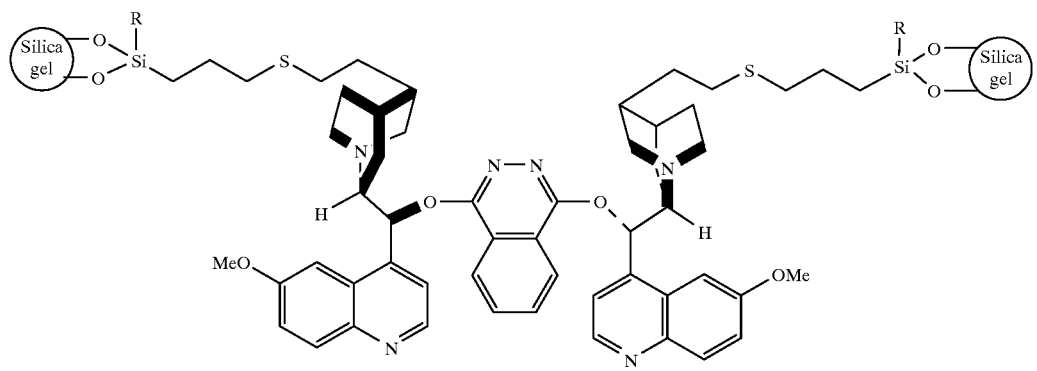
(3)
3. A compound according to claim 1 having the formula:
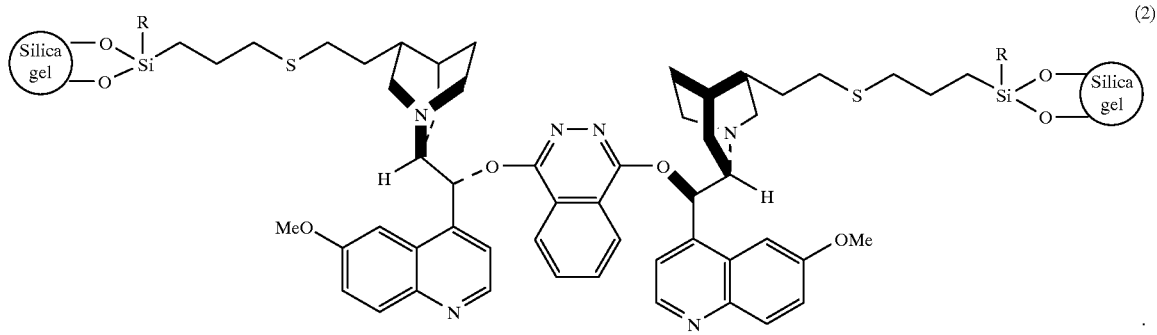
(2)
4. A compound according to claim 1 having the formula:
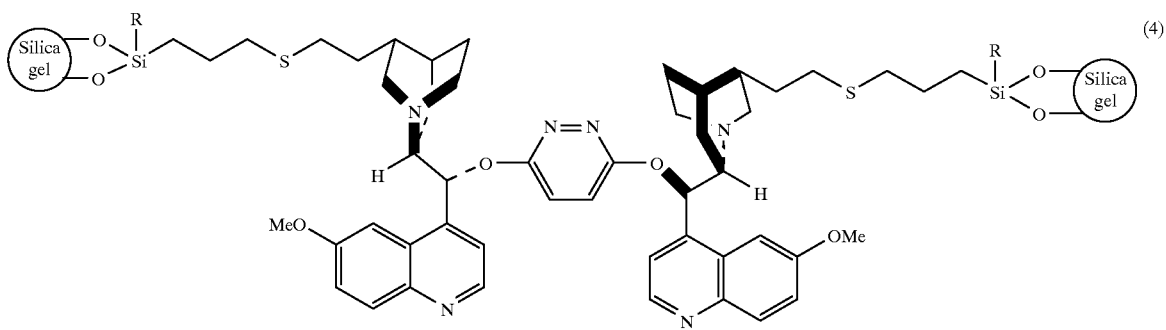
(4)
5. A compound according to claim 1 having the formula:

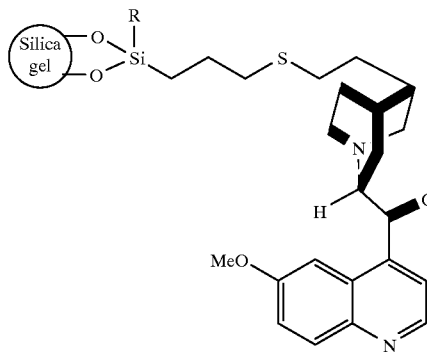
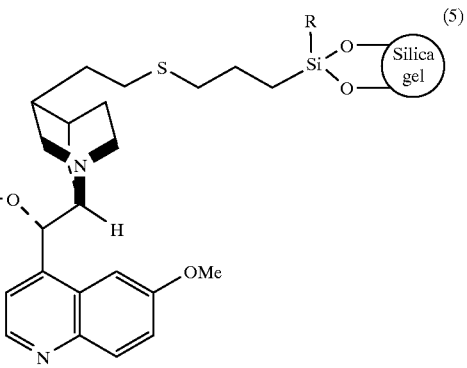

6. A method of preparing silica gel supported bis-cinchona alkaloid compounds represented by formula 8 by reacting a bis-cinchona alkaloid of formula 6 as a chiral monomer with a mercaptopropyl silanized silica gel of formula 7 in an organic solvent in the presence of the free-radical initiator 2,2'-azobis isobutyronitrile

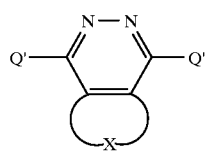

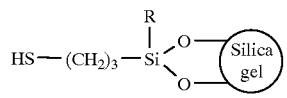

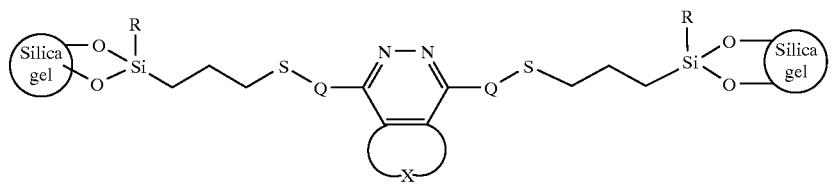

wherein Q is hydroquininyl or hydroquinindinyl; Q' is quininyl or quinidinyl; X is a moiety having 4 carbon atoms; and R is methoxy, ethoxy or methyl.

7. The method according to claim 6, wherein the organic solvent is chloroform and the bis-cinchona alkaloid derivative of the formula 6 and mercaptopropyl silanized silica gel of the formula 7 are reacted in the equivalent weight ratio of 1:2.

8. A method of preparing silica supported bis-cinchona alkaloid compounds according to claim 6, wherein X is a portion of an unsaturated cyclic compound, and said unsaturated cyclic compound is selected from the group consisting of pyridazine and phthalazine.

9. A method of preparing silica gel supported bis-cinchona alkaloid compounds represented by formula II by reacting a bis-cinchona alkaloid of formula 9 as a chiral monomer with a mercaptopropyl silanized silica gel of formula 10 in an organic solvent in the presence of the free-radical initiator 2,2'-azobis isobutyronitrile

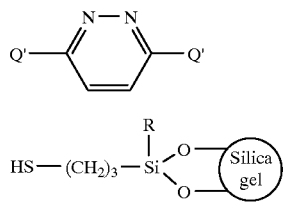
(9)
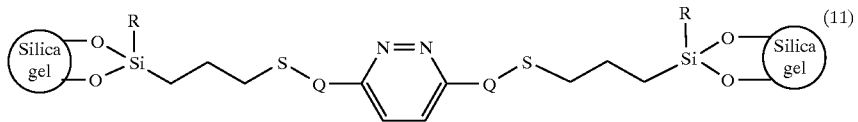
(10)
(11)
wherein Q is dihydroquininyl or dihydroquinindinyl; Q' is quininyl or quinidinyl; and R is methoxy, ethoxy or methyl.
10. Silica gel supported bis-cinchona alkaloid compounds according to claim 1, wherein X is a portion of an unsaturated cyclic compound, and said unsaturated cyclic compound is selected from the group consisting of pyridazine and phthalazine.
* * * * *